United States Patent [19]

Whitney et al.

[11] 4,220,776

[45] Sep. 2, 1980

[54] N-(PYRIDOTHIENOPYRAZOL)AMIDES

[75] Inventors: Joel G. Whitney, Kennett Square, Pa.; Edward C. Hermann, Newark, Del.

[73] Assignee: E. I. Du Pont de Nemours and Company, Wilmington, Del.

[21] Appl. No.: 970,732

[22] Filed: Dec. 21, 1978

Related U.S. Application Data

[63] Continuation-in-part of Ser. No. 885,252, Mar. 10, 1978, abandoned.

[51] Int. Cl.$^2$ ............................................. C07D 495/14
[52] U.S. Cl. ..................................... 546/83; 424/256; 546/114; 546/298
[58] Field of Search ........................... 546/83; 424/256

[56] References Cited

U.S. PATENT DOCUMENTS

| | | | |
|---|---|---|---|
| 3,887,570 | 6/1975 | Denzel et al. | 546/83 |
| 4,018,790 | 4/1977 | Paget et al. | 424/248.5 X |
| 4,104,275 | 8/1978 | Kaver | 260/340.3 X |
| 4,138,566 | 2/1979 | Krimmel | 544/357 |
| 4,140,785 | 2/1979 | Hoffman et al. | 548/359 |

OTHER PUBLICATIONS

Hoffmann, C., Virus Chemo Therapy-Today (Text of Lecture Presented at PTO 10-12-77).
March, J., *Advanced Organic Chemistry*, McGraw Hill, New York, 1968, p. 335.

*Primary Examiner*—Henry R. Jiles
*Assistant Examiner*—Richard A. Schwartz

[57] ABSTRACT

Certain N-(pyridothienopyrazol)amides such as 2,2-diethyl-N-[1-methyl-1H-pyrazolo(3',4':4,5)thieno-(2,3-b)pyridin-3-yl]butanamide are useful for the prophylaxis and therapy of diseases caused by rhinoviruses.

10 Claims, No Drawings

N-(PYRIDOTHIENOPYRAZOL)AMIDES

CROSS REFERENCE TO RELATED APPLICATIONS

This application is a continuation-in-part to application Ser. No. 885,252 filed Mar. 10, 1978, now abandoned.

BACKGROUND OF THE INVENTION

This invention is directed to a class of novel compounds and to the use of those compounds for the treatment of diseases in mammals caused by rhinoviruses.

Unlike many other infectious agents, viruses are intracellular parasites, the functions of which necessarily involve the metabolic processes of the invaded cell. For this reason, agents that inhibit or kill viruses are likely to cause injury to the host cell as well. Thus, the development of effective antiviral agents presents even more difficulty than the search for drugs to combat diseases caused by other microorganisms.

Over the course of many years, thousands of compounds have been evaluated in the search for effective agents. Very few compounds ever reach the stage of clinical testing and of these only a small number have been developed commercially. One of the best known of these agents is 1-aminoadamantane hydrochloride, which has been found to be effective for the prophylaxis and symptomatic treatment of illness caused by influenza A virus strains. Idoxuridine and adenine arabinoside are effective for the topical treatment of herpes simplex keratitis. Methisazone has been found to be effective for the prevention of smallpox; however, it is not widely used because of the virtually complete elimination of smallpox through innoculation with vaccines.

There is clearly a great need in this day and age for a compound that will be effective against rhinoviruses; the causative agents of most common colds. This need is of critical importance to the elderly and chronically ill for whom rhinovirus infections can often be dangerous. Moreover, the absenteeism and reduced ability to perform effectively, occasioned by the common cold in humans, represent an astronomical waste of resources. Thus, the need of modern society for an agent which is effective against rhinoviruses is of primary importance.

BRIEF SUMMARY OF THE INVENTION

The invention is, therefore, directed to a novel class of N-(pyridothienopyrazol)amides which are intended for use in the treatment or prevention of the "common cold", an upper respiratory disease of man characterized by rhinorrhea, nasal congestion, sneezing, pharyngeal discomfort, and cough[1]. More particularly, these novel compounds are antirhinoviral agents, inhibiting the multiplication of rhinoviruses, the causative agents of most colds. In contrast to drugs used for symptomatic relief of colds, these compounds inhibit the production of the infectious agent, i.e., one or more of the over one-hundred known strains of rhinovirus. Many of these compounds are also active against certain other picornaviruses. In particular, the invention is directed to compounds corresponding to the formula

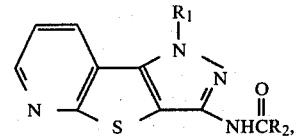

wherein
$R_1$ is methyl or ethyl;
$R_2$ is selected from cyclohexyl, benzyl, 3-pyridyl, 1-adamantyl, $C_{2-5}$ haloalkyl having 1-3 halogen substituents in other than the α-position with respect to the carbonyl group, and the groups:

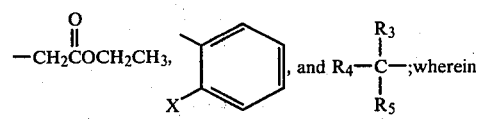

X is H, F, Cl;
$R_3$ and $R_4$ are independently selected from H and $C_{1-3}$ alkyl; and
$R_5$ is selected from H and $C_{1-5}$ alkyl; and their pharmaceutically suitable acid addition salts, such as hydrochloride or sulfate.

[1] Evan, A. S., Ed., *Viral Infections of Humans*, Plenum Publishing Co., New York, N.Y. (1976) pp. 383–408.

The invention is also directed to pharmaceutical compositions containing the above-described compounds and to the method of using them for the prophylaxis and therapy of diseases caused by rhinoviruses in mammals.

DETAILED DESCRIPTION OF THE INVENTION

Within the context of the above formula, it has been found that certain structural variations are preferred because of the indication of greater antiviral effectiveness.

In particular, it is preferred that $R_1$ be methyl and/or that $R_2$ be selected from the group consisting of 3-pyridyl, chloroalkyl, and a group

in which $R_3$ and $R_4$ are independently $C_{1-3}$ alkyl and $R_5$ is H or $C_{1-5}$ alkyl. Still further preferred are those compounds in which $R_2$ is

and the R groups are selected from one of the following:
$R_3$, $R_4$ and $R_5$ are each methyl;
$R_3$ is H, $R_4$ is ethyl, and $R_5$ is butyl;
$R_3$, $R_4$ and $R_5$ are each ethyl; or
$R_3$ and $R_4$ are ethyl and $R_5$ is H.

The most preferred compounds are: 2, 2-diethyl-N-[1-methyl-1H-pyrazolo(3′,4′:4,5)thieno(2,3-b)pyridin-3-yl]-butanamide; and 2-ethyl-N-[1-methyl-1H-pyrazolo(3′,4′:4,5)thieno(2,3-b)pyridin-3-yl]hexanamide.

Synthesis

The compounds of this invention are made by the following sequence of reactions:

SCHEME 1

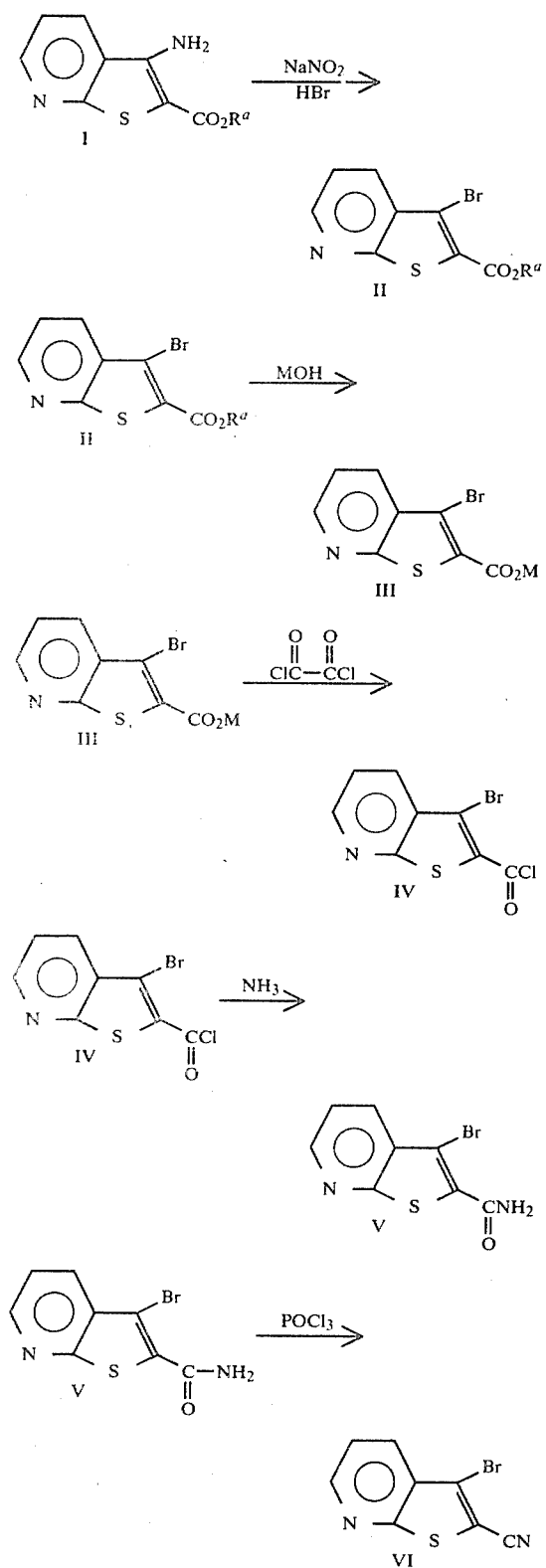

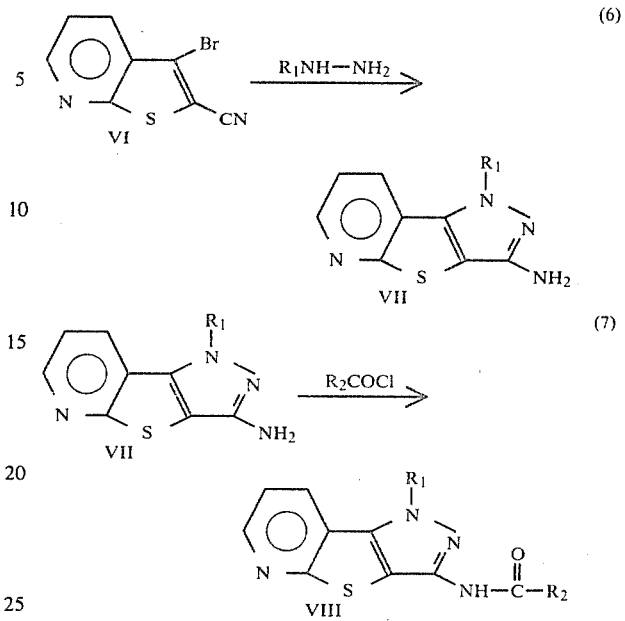

In the foregoing reaction sequence, Scheme I, $R^a$ is a lower ($C_{1-4}$) alkyl group which is preferably methyl or ethyl and MOH is an aqueous alkali metal hydroxide which is preferably potassium hydroxide.

Reaction (1) is both a diazotiation and diazo salt decomposition reaction which, because of its highly exothermic nature, is preferably carried out at low temperatures with agitation. Preferred temperatures are 0°–10° C. However, it will be recognized that the reaction could be carried out at higher temperatures by introducing the reactant at a slower rate in order for the exotherm to become dissipated. In reaction (1), other nitrites may be used to effect diazotization. This reaction step is of particular interest, however, from the standpoint that, by analogy with similar aromatic amines, it would be expected to produce the corresponding hydroxyl compound, not the bromine-substituted material. The starting material for Reaction (1), I, is described in *J. Het. Chem.*, 11, 975 (1974)

Reaction (2) is a hydrolysis reaction, which can be carried out with either an acid or, as illustrated above, with a base. Preferred bases include NaOH and KOH of which the latter is especially preferred.

The hydrolyzed product of Reaction (2) is then converted to 3-bromothieno(2,3-b)pyridine-2-carboxamide. In the route shown above, the acid is converted to an acid halide (Reaction 3), which in turn is converted to the corresponding carboxamide by ammonalysis (Reaction 4). The intermediate carboxylic acid halides can be prepared by reaction of the carboxylic acid with inorganic halides such as thionyl chloride or alternatively by reaction of the carboxylic acid or alkali metal salt with oxalyl chloride or bromide. Mixed anhydrides of the carboxylic acid can be prepared with alkyl chloroformates, and subsequently converted to the amide.

Alternatively, ethyl 3-bromothieno(2,3-b)pyridine-2-carboxylate could be transformed directly to the corresponding carboxamide by ammonolysis, as follows:

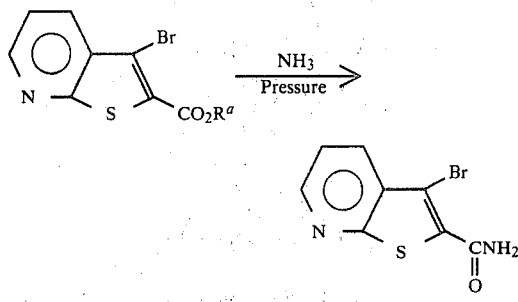

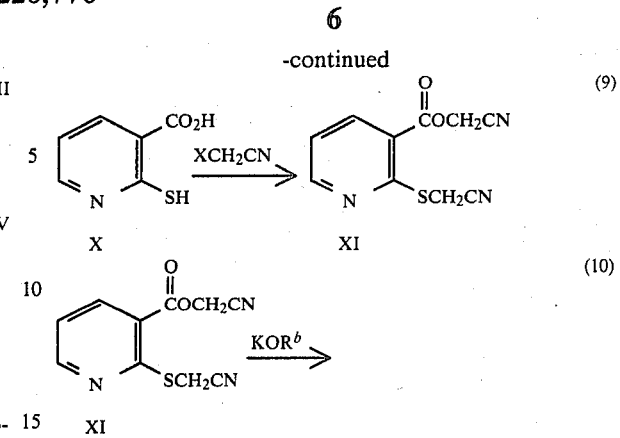

Reaction (5) is a dehydration step by which 3-bromo-thieno(2,3-b)pyridine-2-carboxamide is converted to the corresponding carbonitrile. A preferred reagent for this purpose is POCl₃.

Alternatively, the carboxylic acid can be reacted with chlorosulfonyl isocyanate to form the carbonitrile directly as follows:

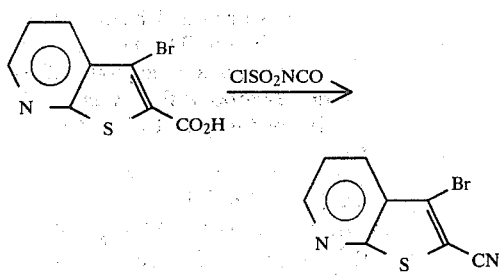

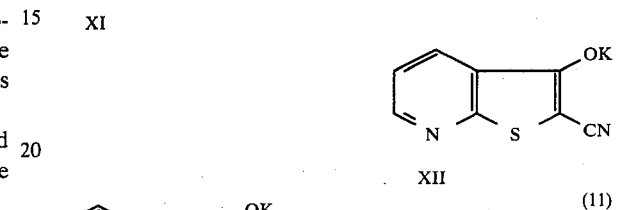

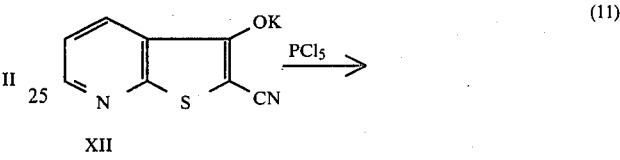

In Reaction (6), the above-described 2-carbonitrile compound (VI) is reacted with methyl- or ethylhydrazine in solution to form 1-methyl- or 1-ethyl-1H-pyrazolo(3',4':4,5)thieno(2,3-b)pyridin-3-amine. For suitable reaction rates, it is preferred to carry out this reaction at 50°–100° C. in an inert organic solvent such as dimethylsulfoxide.

In the final step of the process, the 3-amine-substituted product (VII) is acylated to convert the amine group to an appropriate amide derivative (VIII). The amine can be acylated with carboxylic acid chlorides, bromides, anhydrides or esters using any of several standard procedures which are well known in the art. Reaction (7) can be carried out in an inert organic solvent, such as methylene chloride, tetrahydrofuran, or dimethylformamide, or without added solvent, using the acylating agent as solvent, such as acetic anhydride; the reaction temperature is not critical and can range between 0° C. and the boiling point of the solvent or reaction mixture. The use of an acid acceptor such as pyridine is preferred when Reaction (7) is carried out with a carboxylic acid halide.

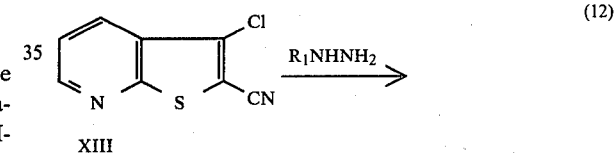

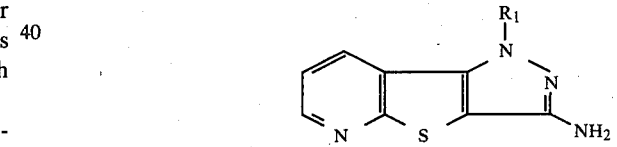

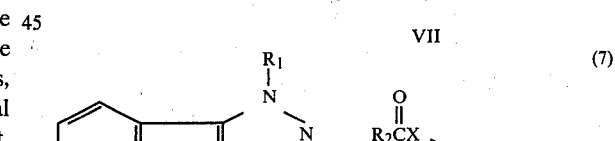

SCHEME II

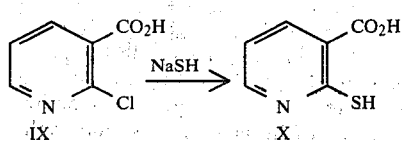

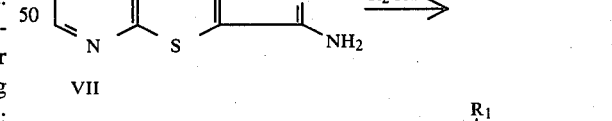

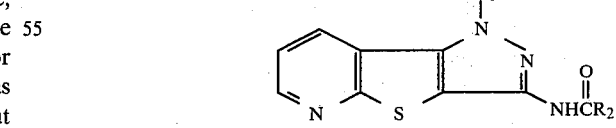

In the foregoing reaction sequence (Scheme II), X is a halogen (Cl, Br or I) and $R^b$ is an alkyl group which is ethyl or tert-butyl.

Reaction (8) is a nucleophilic displacement by thiolate on readily available chloronicotinic acid IX. IX can be alkylated and esterified in one step (Reaction (9)) by treatment with ICH₂CN, ClCH₂CN/KI or BrCH₂CN under basic conditions, preferably KHCO₃. Reaction (9) is novel and labor-saving in that both the alkylation and esterification of X is carried out in one reaction step. The cyclization step, Reaction (10), is straight forward, giving the readily isolated potassium oxide XII. Upon heating the potassium oxide XII with PCl₅ a displacement takes place to give the key intermediate XIII, which readily reacts with the alkylhydrazine to give the amine VII in high yield. With Reaction (12) Schemes I and II converge, and the acylation of VII is carried out according to Reaction (7).

Using 1-methyl- or 1-ethyl-1H-pyrazolo(3',4':5,4)-thieno(2,3-b)pyridin-3-amine and the appropriate acylating agent, the compounds listed below can be prepared by the procedures of Examples 1, 2 and/or 3 herein below:

N-[1-methyl-1H-pyrazolo(3',4':4,5)thieno(2,3-b)pyridin-3-yl]cyclohexanecarboxamide N-[1-ethyl-1H-pyrazolo(3',4':4,5)thieno(2,3-b)pyridin-3-yl]benzamide 3-chloro-N-[1-methyl-1H-pyrazolo-(3',4':4,5)thieno(2,3-b)pyridin-3-yl]propionamide N-[1-ethyl-1H-pyrazolo(3',4':4,5)thieno(2,3-b)pyridin-3-yl]6,6,6-trifluorohexanamide 3,3'-dichloro-2,3-dimethyl-N-[1-methyl-1H-pyrazolo(3',4':4,5)thieno(2,3-b)pyridin-3-yl]propionamide N-[1-ethyl-1H-pyrazolo(3',4':4,5)thieno(2,3-b)pyridin-3-yl]hexanamide 2-ethyl-N-[1-methyl-1H-pyrazolo(3',4':4,5)thieno-2,3-b)pyridin-3-yl]butanamide 3,3-dimethyl-N-[1-methyl-1H-pyrazolo(3',4':4,5)thieno-2,3-b)pyridin-3-yl]propionamide 2,2-dimethyl-N-[1-ethyl-1H-pyrazolo(3',4':4,5)thieno-2,3-b)pyridin-3-yl]valeramide 2-ethyl-2-methyl-N-[1-methyl-1H-pyrazolo(3',4':4,5)-thieno(2,3-b)pyridin-3-yl]propionamide 2,4-dimethyl-2-ethyl-N-[1-ethyl-1H-pyrazolo(3',4':4,5)-thieno(2,3-b)pyridin-2-yl]valeramide 2-ethyl-2-methyl-N-[1-methyl-1h-pyrazolo(3',4':4,5)-thieno(2,3-b)pyridin-3-yl]butanamide

EXAMPLE 1

2,2-Diethyl-N-[1-methyl-1H-pyrazolo(3',4':4,5)-thieno(2,3-b)pyridin-3-yl]butanamide A solution of 14.0 g of sodium nitrite in 50 ml of H₂O was added dropwise to a stirred suspension of 53.9 g of ethyl 3-aminothieno(2,3-b)pyridine-2-carboxylate [*J. Het. Chem.*, 11 975 (1974)] in 250 ml of 48% hydrobromic acid cooled at 5° C. The reaction mixture was allowed to warm to room temperature and was stirred for an additional hour. The insoluble hydrobromide salt of ethyl 3-bromothieno(2,3-b)pyridine-2-carboxylate was collected by filtration, washed with acetone and air dried to give 40.8 g of product.

A small sample was distributed between 10% aqueous sodium bicarbonate and methylene chloride. The organic layer was dried over magnesium sulfate and evaporated to give ethyl 3-bromothieno(2,3-b)pyridine-2-carboxylate, m.p. 100°–102°. NMR (CDCl₃)δ1.2 (t, 3); 4.2 (q, 4); 7.3–7.5 (m, 1); 8.0–8.2 (m, 1); 8.5–8.8 (m, 1).

Anal. Calcd. for C₁₀H₈BrNO₂S: C, 41.96; H, 2.80; N, 4.90. Found: C, 42.19; H, 2.88; N, 5.37.

The hydrobromide salt was suspended in 550 ml of ethanol and the mixture heated to 45° C. A solution of 22.0 g of potassium hydroxide in 400 ml of ethanol was added and the reaction was stirred several hours at room temperature. The potassium salt of 3-bromothieno(2,3-b)pyridine-2-carboxylic acid was collected by filtration and dried overnight at 80° C. under vacuum to give 44.0 g of product.

A small sample was dissolved in water and the solution acidified with acetic acid. A precipitate of 3-bromothieno(2,3-b)pyridine-2-carboxylic acid. m.p. 247°–248° C., was collected by filtration.

Anal. Calcd. for C₈H₄BrNO₂S: C, 37.21: H, 1.55; N, 5.43. Found: C, 37.56; H, 2.20: N, 5.46.

The potassium salt (42.4 g) was suspended in 650 ml of dry benzene and 30.0 g of oxalyl chloride was added dropwise. The reaction mixture was stirred and heated at reflux for one hour. Excess oxalyl chloride was removed by distillation at atmospheric pressure and the hot pot residue was added to a stirred mixture of 130 ml of concentrated ammonium hydroxide and ice. The precipitated 3-bromothieno(2,3-b)pyridine-2-carboxamide was collected by filtration and dried overnight at 80° C. under vacuum to give 23.0 g of product, m.p. 266°–268° C.

Anal. Calcd. for C₈H₅BrN₂OS: C, 37.35, H, 1.95; N, 10.89. Found: C, 37.60: H, 2.11; N, 10.97.

A suspension of 18.1 g of the amide in 125 ml of phosphorus oxychloride was stirred and heated at reflux for 3 hours to give a solution. The hot reaction solution was poured into ice and a precipitate of 3-bromothieno(3,2-b)pyridine-2-carbonitrile was collected by filtration and air dried to give 16.3 g of product, m.p. 182.5°–184° C.

Anal. Calcd. for C₈H₃BrN₂S: C, 40.17; H, 1.26; N, 11.71. Found: C, 40.43; H, 1.39; N, 12.14.

A solution of the nitrile in 200 ml of dimethyl sulfoxide was heated with 10.0 g of methylhydrazine at 75°–80° C. overnight. The reaction mixture was allowed to cool to room temperature and was poured into ice water. A precipitate of 1-methyl-1H-pyrazolo(3',4':4,5)thieno(2,3-b)pyridin-3-amine was collected by filtration and dried overnight at 80° C. under vacuum to give 11.7 g of product, m.p. 194°–196° C.

Anal. Calcd. for C₉H₈N₄S: C, 52.94; H, 3.92: N, 27.45. Found: C, 52.88; H, 3.90: N, 27.54.

To a stirred suspension of 4.6 g of the amine in a mixture of 25 ml of pyridine and 125 ml of methylene chloride was added dropwise a solution of 4.2 g of triethylacetyl chloride in 25 ml of methylene chloride. The reaction solution was stirred overnight at room temperature and then washed with 1 N hydrochloric acid, water, 10% aqueous sodium bicarbonate solution and then with water. The organic layer was dried over potassium carbonate and concentrated under vacuum to give 5.2 g of crude product. One recrystallization from carbon tetrachloride gave 3.0 g of 2,2-diethyl-N-[1-methyl-1H-pyrazolo(3',4':4,5)thieno(2,3-b)pyridin-3-yl)butanamide, m.p. 138°–9° C. NMR (CDCl₃) δ 1.0 (t, 3); 1.5–2.1 (m,5); 4.1 (s,3); 6.1–7.45 (m,1); 8.0–8.3 (m, 1);

Anal. Calcd. for C₁₇H₂₂N₄OS: C, 61.82: H, 6.67: N, 17.0. Found: C, 61.42; H, 6.67: N, 17.1.

EXAMPLE 2

2-Ethyl-N-[1-methyl-1H-pyrazolo(3',4':4,5)thieno(2,3-b)-pyridin-3-yl]hexanamide

In a 1 l. flask flushed with nitrogen 66 g of sodium sulfhydrate was added to a solution of 48 g (0.3 mole) of 2-chloronicotinic acid in 200 ml of dimethylformamide. This was heated slowly to 135° C. under nitrogen and then stirred at this temperature for 3 hr. The reaction was cooled to 25° C., an additional 7 g of sodium sulfhydrate added, and the reaction then reheated to 135° for 2.5 hr. The reaction was cooled and concentrated; the solid residue was dissolved in 700 ml of water, acidified to pH 3 with 6 N HCl, saturated with sodium chloride, filtered and washed H$_2$O. The yellow solid was dried under vacuum to give 42 g of 2-mercuptonicotinic acid. m.p. 252°–254° C.(d). NMR (DMSO) δ6.0(bs,1); 6.5(dd,1); 7.6(dd,1); 7.9(dd,1).

12 Grams (0.16 mole) of chloroacetonitrile was added to a stirred suspension of 6.2 g (0.04 mole) of 2-mercaptonicotinic acid, 8.0 g (0.08 mole) of potassium bicarbonate, and 20 g (0.12 mole) of potassium iodide in 100 ml of dimethylformamide at 10° under nitrogen. The reaction was stirred at 10° for 7 hr., then at 25° for 15 hr. The reaction mixture was then poured into water, saturated with sodium chloride and filtered. The resulting solid was dissolved in methylene chloride, dried with magnesium sulfate and evaporated to give 7.5 g of cyanomethyl 2-(cyanomethylthio)nicotinate. m.p. 140°–143° C. NMR (DMSO) δ3.3(s,2); 4.3(s,2); 6.4(dd,1); 7.4(dd,1); 7.8(dd,1).

104.3 Grams (0.447 mole) of cyanomethyl 2-(cyanomethylthio)nicotinate was added to a stirred solution of 55.1 g (0.49 mole) of potassium t-butoxide in 1300 ml of ethanol under nitrogen. This was stirred at 25° for 1 hr.; 1000 ml of ethyl ether was added and the stirring continued for 1 hr. The reaction solid was filtered and washed with ethyl ether to give 92 g of potassium 2-cyanothieno[2,3-b]pyridine-3-oxide. m.p. will add 390° C. (d). NMR (DMSO) δ6.7(dd,1); 7.5(dd,1); 8.0(dd,1).

2.1 Grams (0.01 mole) of potassium 2-cyanothieno[2,3-b]pyridine-3-oxide and 5 g (0.025 mole) of phosphorous pentochloride were suspended in 40 ml of toluene and stirred at 75° for 20 hr under nitrogen. The reaction was cooled, poured into water, and made basic with potassium carbonate. The organic phase was separated, and the aqueous phase extracted with ethyl acetate; the organic phase and ethyl acetate extracts were combined, dried with magnesium sulfate, treated with charcoal, and evaporated to give 1.3 g of 2-cyano-3-chlorothieno[2,3-b]pyridine. m.p. 144°–145° C. NMR (CDCl$_3$) δ7.5(dd,1);

15 Grams (0.066 mole) of 2-cyano-3-chlorothieno(2,3-b)pyridine and 17.5 ml (0.33 mole) of methylhydrazine were dissolved in 110 ml of dimethylsulfoxide and heated to 75° for 15 hr under nitrogen. The reaction was cooled and poured into water. The solid was filtered and dried to give 11 g of 1-methyl-1H-pyrazolo(3',4':4,5)thieno(2,3-b)pyridine-3-amine. m.p. 194°–196° C. NMR(CDCl$_3$) δ4.0(s,3); 5.2(s,2); 7.4(dd,1); 8.4(m,2).

A solution of 5 ml of methylene chloride and 0.95 g (0.059 mole) of (d,l) 2-ethyl hexanoyl chloride was added to a suspension of 1.0 g (0.049 mole) of 1-methyl-1H-pyrazolo(3',4':4,5)thieno(2,3-b)pyridine-3-amine in 25 ml of methylene chloride and 5 ml of pyridine. The reaction was stirred for 12 hr at 25°, then washed successively with 1 N hydrochloric acid, saturated sodium bicarbonate and water. The organic layer was dried with magnesium sulfate and evaporated to a solid which was recrystalized from carbon tetrachloride to give 1.0 g of (d,l)2-ethyl-N-[1-methyl-1H-pyrazolo(3',4':4,5)-thieno(2,3-b)pyridin-3-yl]hexanamide. m.p. 133°–134° C. NMR(CDCl$_3$) δ0.8–2.4(m,15); 4.1(s,3); 7.2(dd,1); 8.1(dd,1); 8.7(dd,1); 8.8(s,1).

EXAMPLE 3

N-[1-Methyl-1H-pyrazolo(3',4':4,5)thieno(2,3-b)pyridin-3-yl]acetamide

A solution of 2.0 g of 1-methyl-1H-pyrazolo(3',4':4,5)thieno(2,3-b)pyridin-3-amine (Example 1) in 50 ml of tetrahydrofuran was heated at reflux with 3.0 g of acetic anhydride for 15 minutes. The reaction solution was cooled and 1.2 g of crystals of N-[1-methyl-1H-pyrazolo(3',4':4,5)thieno(2,3-b)pyridin-3-yl]acetamide, m.p. 306°–8° C., were collected by filtration. NMR (CF$_3$CO$_2$H) δ2.2(s,3); 4.2(s,3); 8.0–8.3(m,1); 8.8–9.3(m,2).

Anal. Calcd. for C$_{11}$H$_{10}$N$_4$OS: C, 53.66; H, 4.07; N, 22.76. Found: C 53,46; H, 4.17.

By the procedures described in Examples 1 or 2 1-methyl-1H-pyrazolo(3',4':4,5)thieno(2,3-b)pyridin-3-amine was reacted with the appropriate acid chlorides to afford compounds of the subject case, for example:

TABLE 1

| Example No. | R$_2$ | Melting Pt. | Recrystallization Solvents |
|---|---|---|---|
| 1 | —C(CH$_2$CH$_3$)$_3$ | 138°–139° | CCl$_4$ |
| 2 | (d,l)—CH(CH$_2$)$_3$CH$_3$ \| CH$_2$CH$_3$ | 133°–134° | CCl$_4$ |
| 3 | —CH$_3$ | 306°–308° | CHCl$_3$ |
| 4 | [phenyl] | 223.5°–224.5° | CCl$_4$/CH$_2$Cl$_2$ |
| 5 | —CH$_2$(CH$_2$)$_3$CH$_3$ | 176.0°–177.5° | CCl$_4$/CH$_2$Cl$_2$ |
| 6 | —CH(CH$_3$)$_2$ | 241°–242° | CCl$_4$/CH$_2$Cl$_2$ |
| 7 | [thienyl] | 254°–256° | CCl$_4$/CH$_2$Cl$_2$ |
| 8 | [F-phenyl] | 222.0°–223.5° | CHCl$_3$ |
| 9 | —C(CH$_3$)$_3$ | 214°–215° | CCl$_4$/CH$_2$Cl$_2$ |
| 10 | [pyridyl] | 255°–256° | CCl$_4$ |
| 11 | —CH(CH$_2$CH$_3$)$_2$ | 195.0°–197.0° | CCl$_4$/CH$_2$Cl$_2$ |
| 12 | (d,l)—CHCH$_2$CH$_2$CH$_3$ \| CH$_3$ | 178.5°–179.0° | CCl$_4$/CH$_2$Cl$_2$ |
| 13 | —CH$_2$CH(CH$_3$)$_2$ | 239.5°–244.0° | CCl$_4$/CH$_2$Cl$_2$ |
| 14 | (d,l)—CHCH$_2$CH$_3$ \| CH$_3$ | 211.5°–212.0° | CCl$_4$/CH$_2$Cl$_2$ |
| 15 | —CH$_2$CH$_2$Cl | 213.0°–215.0° | CCl$_4$ |
| 16 | —CH$_2$COCH$_2$CH$_3$ | 230°(d) | CHCl$_3$ |
| 17 | —CH$_2$CH$_3$ | 231.0°–231.5° | CHCl$_3$ |
| 18 | —CH$_2$—[phenyl] | 273°–275° | CH$_2$Cl$_2$ |
| 19 | —CH$_2$CH$_2$CH$_3$ | 208.5°–209.0° | CCl$_4$/CH$_2$Cl$_2$ |

TABLE 1-continued

[Structure: pyridothienopyrazole with CH₃ on N, NHCR₂ group]

| Example No. | R₂ | Melting Pt. | Recrystallization Solvents |
|---|---|---|---|
| 20 | −C(CH₃)₂−CHCl₂ | 241.0°–242.0° | CCl₄/CH₂Cl₂ |
| 21 | [adamantyl structure] | 270.0°–271.0° | CCl₄ |

Using the procedure of Examples 1, 2 or 3 with 1-methyl(or 1-ethyl)-1H-pyrazolo(3',4':4,5)thieno(2,3-b)pyridin-3-amine, the following compounds can be prepared:

TABLE 2

[Structure with R₁ on N and NHCR₂ group]

| R₁ | R₂ |
|---|---|
| −CH₃ | −CH₂(CH₂)₃CH₂Cl |
| −CH₃ | −CH₂(CH₂)₃CF₃ |
| −CH₃ | −CH₂(CH₂)₄CH₃ |
| −CH₃ | −CH₂CH₂CH₂CH(CH₃)₂ |
| −CH₂CH₃ | −C(CH₂CH₃)₃ |
| −CH₂CH₃ | −CH(CH₂CH₃)(CH₂CH₂CH₂CH₃) |
| −CH₃ | −CH(CH₂CH₂CH₃)₂ |
| −CH₃ | −C(CH₃)(CH₃)CH₂CH₂CH₃ |
| −CH₃ | −CH(CH₃)CH(CH₃)CH₂CH₃ |

Antiviral Testing

No pharmaceutical agents have been commercially available for the treatment of rhinoviral infection in man (common cold) except for symptomatic treatment. The prevention of colds with biologicals, such as vaccines, is not practical due to the large number of rhinovirus strains which cause colds, at present numbering over 100 different antigenic types. However, the compounds of this invention have been demonstrated in vitro to be broadly active. In fact, no strain has yet been shown to be resistant. Table 3 below contains a list of strains of rhinovirus which have been tested and found to be inhibited by the compounds of this invention.

TABLE 3
RHINOVIRUS TYPES TESTED AND INHIBITED BY N-(pyridothienopyrazol)amides

| Type | Strain |
|---|---|
| 1A | 2060 |
| 1B | B632 |
| 2 | HGP |
| 3 | FEB |
| 5 | Norman |
| 13 | 353 |
| 14 | 1059 |
| 15 | 1734 |
| 39 | 209 |
| 41 | 56110 |
| 51 | F01-4081 |
| Not yet typed | 998 |
| Not yet typed | 1426 |
| Not yet typed | 1492 |
| Not yet typed | 1662 |
| Not yet typed | 4006 |
| Not yet typed | 6579 |

Treatment for individual infections, using formulations well known to the skilled pharmaceutical chemist, may be oral or intranasal; however, oral treatment is the preferred method. An oral dose range, using tablets or capsules, of 2 to 50 mg/kg/dose with doses given as frequently as every 4 hours or as little as once a day, is the suggested regimen of dosing. Pharmaceutical preparations of sustained release compositions can also be used as oral dosage forms.

In using the intranasal route, effective methods include administration by intranasal drops, by nebulizer, or aerosol of useful droplet size. An acceptable range of concentrations is between 0.1 mg/ml and 20 mg/ml, with a preferred range between 0.1 and 2.0 mg/ml.

Gwaltney[2] has demonstrated that hand contact of nasal mucus may be the most important mode of rhinovirus transmission. Sterilization of the hands of people coming into contact with persons infected with rhinovirus would be a method for preventing further spread of the disease. If this class of N-(pyridothienopyrazol)amides were incorporated into a hand washing or hand care procedure they would inhibit production of rhinovirus and decrease the likelihood of the transmission of the disease.

[2]J. Gwaltney, J. O. Hendley and P. Wenzel, N. Engl. J. Med., 288 1361 (1973).

Test Procedures

To those skilled in the art, the following procedure will be recognized as similar to the protocol of Fiala[3], an established method in the field of virology.

[3]Fiala, M., Plaque Formation by 55 Rhinovirus Serotypes, Appl. Microbiol. 16: 1445 (1968).

Rhinovirus-sensitive HeLa cells are grown to confluent monolayers and infected with approximately 100 rhinovirus particles and subsequently covered with an agar-containing medium having varying concentrations of the test chemical. After 3 to 4 days of incubation at 34° C., the agar is removed and the plates stained with crystal violet. The amount of inhibition is determined by the reduction in the number of plaques in the cell layer, the minimum inhibitory composition (MIC) being that concentration of compound required to completely suppress plaque formation.

The compound 2,2-diethyl-N-[1-methyl-1H-pyrazolo(3',4':4,5)thieno(2,3-b)pyridin-3-yl]butanamide (Example 1) was micronized to 2 microns or smaller particle size and suspended in distilled water at series dilutions from 50 μg/ml to 0.4 μg/ml. The results obtained from testing against three rhinovirus strains are shown in Table 4. These results show that the test compound was 100% effective at preventing multiplication of rhinovirus at very low concentration.

Using similar methodology Examples 2–21 were tested and these results shown in Table 4. These compounds all exhibit potent antiviral activity.

TABLE 4

[Structure: pyridothienopyrazole with CH₃ on N, and NHCR₂ group]

Antiviral Activity
(μg/ml); (I₁₀₀)
Rhinovirus Type

| Ex. No. | $R_2$ | 1a | 2 | 39 |
|---|---|---|---|---|
| 10 | [pyridyl] | 2 | 2 | 4 |
| 9 | —C(CH$_3$)$_3$ | 2 | 1 | 1 |
| 6 | —CH(CH$_3$)$_2$ | 10 | 2 | 2 |
| 4 | [phenyl] | 2 | 2 | 2 |
| 5 | —CH$_2$(CH$_2$)$_3$CH$_3$ | 2 | 2 | 2 |
| 2 | (d,l)—CH(CH$_2$)$_3$CH$_3$ \| CH$_2$CH$_3$ | 0.4 | 0.4 | 0.4 |
| 7 | [thienyl/thiacyclohexyl] | 2 | 2 | 2 |
| 8 | [o-fluorophenyl] | 10 | 2 | 2 |
| 1 | —C(CH$_2$CH$_3$)$_3$ | 1 | 0.5 | 0.5 |
| 11 | —CH(CH$_2$CH$_3$)$_2$ | 2 | 2 | 2 |
| 12 | (d,l)—CHCH$_2$CH$_2$CH$_3$ \| CH$_3$ | 2 | 2 | 2 |
| 13 | —CH$_2$CH(CH$_3$)$_2$ | 2 | 2 | 10 |
| 14 | (d,l)—CHCH$_2$CH$_3$ \| CH$_3$ | 2 | 2 | 2 |
| 15 | —CH$_2$CH$_2$Cl | 2 | 2 | 10 |
| 16 | —CH$_2$COCH$_2$CH$_3$ | 10 | 10 | 50 |
| 17 | —CH$_2$CH$_3$ | 10 | 2 | 50 |
| 18 | —CH$_2$—[phenyl] | 50 | 10 | 50 |
| 19 | —CH$_2$CH$_2$CH$_3$ | 2 | 2 | 10 |
| 20 | CH$_3$ \| —CCHCl$_2$ \| CH$_3$ | 0.4 | 0.4 | 0.4 |

TABLE 4-continued

[Structure: pyridothienopyrazole with CH₃ on N, and NHCR₂ group]

Antiviral Activity
(μg/ml); (I₁₀₀)
Rhinovirus Type

| Ex. No. | $R_2$ | 1a | 2 | 39 |
|---|---|---|---|---|
| 21 | [adamantyl] | 10 | .4 | 10 |
| 3 | —CH$_3$ | 16 | 16 | 32 |

Dosage Forms

The compounds of this invention may be employed in useful pharmaceutical compositions such as oral dosage forms, e.g. tablets, hard gelatin capsules, soft gelatin capsules and aqueous suspensions, and intranasal drops.

Used orally, the compounds of this invention will have a therapeutic dose range in man from 2.0 to 300 mg/kg/day. The dosage forms described below are designed to deliver this therapeutic dose.

EXAMPLE 22

The following example demonstrates that the class of N-(pyridothienopyrazol)amides of this invention would be effective in entering mammalian tissue at the sites of rhinovirus infection and replication. 2,2-Diethyl-N-[1-methyl-1H-pyrazolo(3',4':4,5)thieno(2,3-b)pyridin-3-yl]butanamide (Example 1), after oral administration, appears at the site of rhinovirus infections, the respiratory tissue, in concentrations in excess of those required for antirhinovirus activity. This was demonstrated in an experiment in which five overnight-fasted Rhesus monkeys (Mucaca mullata), each weighing 2.5–3 kg, were administered the compound via gastric intubation of a 1 mg/ml aqueous suspension at a dose of 10 mg/kg. One animal was sacrificed at each of the following times after dosing: 0.25, 0.5, 1, 2, and 4 hours. One additional untreated animal was sacrificed for control tissue.

The amount of the compound of Example 1 in the lung tissue at each of these times was determined using a liquid chromatography assay, specific for the unchanged compound. The results in Table 5 show that the level of compound present in the lung tissue, expressed as micrograms of compound per gram of lung, exceeded the in vitro antirhinovirus MIC (approximately 0.5 μg/ml) for at least 2 hours after the compound was administered.

TABLE 5

| Hours After Dosing | Example 1 Concentration in Lung Tissue (μg/g) |
|---|---|
| 0 | 0 |
| 0.25 | 1.1 |
| 0.5 | 1.6 |
| 1 | 2.2 |
| 2 | 1.4 |
| 4 | 0.3 |

EXAMPLE 23

Hard gelatin capsules can be prepared by filling standard two-piece hard gelatin capsules with the following mixture using conventional encapsulating equipment:

| Active Ingredient | 200 mg. |
|---|---|
| Lactose | 225 mg. |
| Talc | 25 mg. |
| Magnesium Stearate | 8 mg. |

EXAMPLE 24

The following mixture is prepared and injected in gelatin by means of a positive displacement pump to form soft gelatin capsules; the capsules are washed in petroleum ether and dried.

| Active Ingredient | 200 mg. |
|---|---|
| Polysorbate 80 | 150 mg. |
| Glycerin | 15 mg. |
| Purified Water | 8 mg. |

EXAMPLE 25

Tablets can be prepared by conventional procedures so that each tablet will contain:

| Active Ingredient | 200 mg. |
|---|---|
| Spray Dried Lactose | 300 mg. |
| Microcrystalline Cellulose | 30 mg. |
| Polyvinylpyrrolidone | 3 mg. |
| Magnesium Stearate | 4 mg. |

EXAMPLE 26

An aqueous suspension for oral administration is prepared so that each 5 ml. contains:

| Active Ingredient | 200 mg. |
|---|---|
| Carboxy methyl cellulose | 5 % |
| Syrup | 35 % |
| Glycerin | 10 % |
| Sorbitol | 10 % |
| Methyl Cellulose | 5 % |
| Sodium Benzoate | 5 mg. |
| Flavor | .1 % |
| Water Q.S. | 5 cc. |

In practicing the intranasal route, effective methods include administration by intranasal drops, by nebulizer or aerosol. An acceptable range of concentrations is between 0.1 mg/ml and 20 mg/ml, with a preferred range between 1.0 and 2.0 mg/ml. The following examples are designed to deliver this effective dose.

EXAMPLE 27

| Intranasal Drops | |
|---|---|
| Active Ingredient | 1.0 mg/ml |
| Surfactant | 0.05 mg/ml |
| Propylene Glycol 50 | } qs 1 ml |
| Ethanol 50 | |

EXAMPLE 28

| Nebulizer | |
|---|---|
| Active Ingredient | 1.0 mg/ml |
| Surfactant | 0.05 mg/ml |
| Ethanol 10 | } qs 1 ml |
| Water 90 | |
| Aerosol | |
| Active Ingredient | 1.0 mg/ml |
| Surfactant | 0.05 mg/ml |
| Ethanol 10 | } qs 1 ml |
| Water 40 | |
| Propellant 50 | |

The compounds of this invention may be employed in useful pharmaceutical compositions such as hand disinfectants, e.g. lotion or rinse. Used topically, the compounds of this invention will have a therapeutic range from 0.1% to 10% in suitable carrier. The dosage forms described below are designed to deliver this therapeutic dose.

EXAMPLE 29

A medicated rinse can be prepared by mixing the following ingredients:

| Active Ingredient | (10%) |
|---|---|
| Glycerin | 10% |
| Ethyl Alcohol | 30% |
| Purified Water | QS to 100% |

EXAMPLE 30

A medicated lotion can be prepared by mixing the following ingredients:

| Active ingredient | (10%) |
|---|---|
| Gum Thickener-Sodium carboxymethyl cellulose | 1% |
| Propylene glycol | 5% |
| Glyceryl monostearate | 5% |
| Lanolin | 5% |
| Ethyl Alcohol | 25% |
| Purified Water | QS to 100% |

It will be recognized by those skilled in the art that a wide variety of other pharmaceutical carriers, diluents, and additives can be used. These are described in "Remington's Pharmaceutical Sciences" by E. W. Martin, a well-known reference in this field.

What is claimed is:

1. A compound of the formula

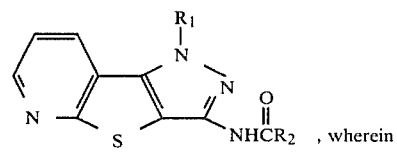

, wherein $R_1$ is methyl or ethyl;
$R_2$ is selected from cyclohexyl, benzyl, 3-pyridyl, 1-adamantyl, $C_{2-5}$ haloalkyl having 1–3 halogen substituents in other than the α-position with respect to the carbonyl group, and the groups —$CH_2CO_2C_2H_5$, 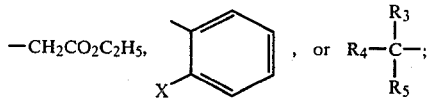, or 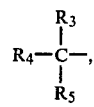;

wherein
X is H, Cl, or F;
$R_3$ and $R_4$ are independently selected from H and $C_{1-3}$ alkyl; and
$R_5$ is selected from H and $C_{1-5}$ alkyl; or a pharmaceutically suitable acid addition salt.

2. A compound of claim 1 in which $R_1$ is methyl.
3. A compound of claim 1 in which $R_2$ is 3-pyridyl.
4. A compound of claim 1 in which $R_2$ is chloroalkyl.
5. A compound of claim 1 in which $R_2$ is wherein $R_3$ and $R_4$ are independently $C_{1-3}$ alkyl, and $R_5$ is H or $C_{1-5}$ alkyl.

6. A compound of claim 5 in which $R_3$, $R_4$ and $R_5$ are methyl.
7. A compound of claim 5 in which $R_3$, $R_4$ and $R_5$ are ethyl.
8. A compound of claim 5 in which $R_3$, $R_4$ are ethyl and $R_5$=H.
9. The compound 2,2-diethyl-N-[1-methyl-1H-pyrazolo(3',4':4,5) thieno(2,3-b)pyridin-3-yl]butanamide
10. The compound 2-ethyl-N-[1-methyl-1H-pyrazolo(3',4':4,5)thieno(2,3-b)pyridin-3-yl]hexanamide.

* * * * *